United States Patent [19]
Greenhut

[11] Patent Number: 5,964,788
[45] Date of Patent: Oct. 12, 1999

[54] METHOD AND APPARATUS FOR CONTROLLING A PACEMAKER USING RESPIRATION

[75] Inventor: Saul E. Greenhut, Aurora, Colo.

[73] Assignee: Pacesetter, Inc., Sylmar, Calif.

[21] Appl. No.: 08/959,391

[22] Filed: Oct. 28, 1997

[51] Int. Cl.⁶ ............................ A61N 1/365; A61N 1/362
[52] U.S. Cl. ................................. 607/17; 607/20; 607/18
[58] Field of Search ............................................. 607/17–20

[56] References Cited

U.S. PATENT DOCUMENTS

| | | | |
|---|---|---|---|
| 4,722,342 | 2/1988 | Amundson | 607/20 |
| 4,901,725 | 2/1990 | Nappholz . | |
| 5,356,425 | 10/1994 | Bardy et al. | 607/14 |
| 5,441,523 | 8/1995 | Nappholz . | |
| 5,441,524 | 8/1995 | Rueter et al. | 607/18 |
| 5,524,632 | 6/1996 | Stein et al. . | |
| 5,540,727 | 7/1996 | Tockman et al. . | |
| 5,562,712 | 10/1996 | Steinhaus . | |
| 5,755,740 | 5/1998 | Nappholz | 607/18 |

OTHER PUBLICATIONS

Assessment of Automatic Regulation in Chronic Congestion Heart Failure By Heart Rate Spectral Analysis (Am. J. Cardiol 1988; 61: 1292–1299) Saul, et al.

Sobh, et al. Altered Cardiorespiratory Control in Patients With Severe Congestive Heart Failure: A Transfer Function Analysis Approach; IEEE Computers in Cardiology 0276–6547/96, pp. 33–36.

Hayano et al. Respiratory Sinus Arrythmia, Circulation, vol. 94, No. 4, Aug. 15, 1996.

Saul et al. Nonlinear Interactions Between Respiration and Heart Rate: Classical Physiology or Entrained Nonlinear Oscillators; IEEE Computers in Cardiology 0276–6574/89/0000/0299, 1989, pp. 299–302.

Huikuri, et al. Frequency Domain Measures of Heart Rate Variability Before Onset of Non–Sustained and Sustained Ventricular Tachycardia Circulation vol. 87, 1804, Apr. 1993, pp. 1220–1228.

Circulation (Circ 1996;94:842–847.

*Primary Examiner*—William E. Kamm
*Assistant Examiner*—Carl H. Layno
*Attorney, Agent, or Firm*—Tiberiu Weisz; Gottlieb, Rackman & Reisman, P.C.

[57] ABSTRACT

In an implantable pacemaker the pacing rate is adjusted in synchrony with the respiration of the patient to thereby mimic respiratory sinus arrhythmia noted in healthy patients. Preferably, first a metabolic demand parameter pacing parameter is derived from a metabolic demand of the patient, such as minute volume, and then this parameter is adjusted using a respiration detector. The adjustment may be made dependent on the exercise level of the patient, his age and his physical fitness.

46 Claims, 10 Drawing Sheets

METHOD AND APPARATUS FOR CONTROLLING A PACEMAKER USING RESPIRATION

BACKGROUND OF THE INVENTION a. Field of the Invention

This invention relates to rate-responsive pacemakers and, more particularly, to pacemakers that employ a respiration sensor as a metabolic rate indication and uses the respiration as a means of controlling their pacing. More particularly, the present invention pertains to a pacemaker wherein a rate responsive parameter is derived from said metabolic rate indication, said parameter being modified synchronously with respiration.

b. Description of the Prior Art

Many attempts have been made to control the heart rate of a pacemaker patient so that it will duplicate the intrinsic heart rate of a healthy person both when the patient is at rest and when the patient is involved in various levels of exercise. Metabolic demand related parameters heretofore proposed for controlling the pacing rate include the QT interval, respiration rate, venous oxygen saturation, stroke volume, venous blood temperature, and minute volume or ventilation, among others. (The terms minute ventilation and minute volume are used interchangeably). In addition, the use of mechanical sensors which detect patient motion have also been explored in such attempts at achieving improved rate-responsiveness.

Of the various parameters available, it has been found that pacemakers using minute volume as a parameter for controlling pacing rate are particularly advantageous.

It has been observed that one of the short term physiological activities which affect the intrinsic heart rates of healthy individuals is respiration. This phenomenon, referred to as Respiratory Sinus Arrhythmia (RSA), is a well known phenomenon which has been described in the literature in 1847. See Saul et al. ASSESSMENT OF AUTOMATIC REGULATION IN CHRONIC CONGESTIVE HEART FAILURE BY HEART RATE SPECTRAL ANALYSIS (Am. J. Cardiol 1988; 61:1292–1299). Sobh et al. ALTERED CARDIORESPIRATORY CONTROL IN PATIENTS WITH SEVERE CONGESTIVE HEART FAILURE: A TRANSFER FUNCTION ANALYSIS APPROACH; IEEE Computers in Cardiology 0276-6547/96, p. 33–36 1996; Hayano et al. RESPIRATORY SINUS ARRHYTHMIA, Circulation, Vol. 94, No. 4, Aug. 15, 1996; Saul et al. NONLINEAR INTERACTIONS BETWEEN RESPIRATION AND HEART RATE: CLASSICAL PHYSIOLOGY OR ENTRAINED NONLINEAR OSCILLATORS; IEEE Computers in Cardiology 0276-6574/89/0000/0299, 1989, p. 299–302.

In normal individuals the heart rate varies in response to autonomic as well as other regulatory inputs to the sinoatrial (SA) node. The highest frequency variations are a result of parasympathetic input and are modulated by respiration. For this reason, heart rate variation in the greater than 0.15 Hz range is commonly referred to as respiratory sinus arrhythmia (RSA). Although referred to as an arrhythmia, this rate variation with respiration has been found to be important to survival (i.e., individuals without RSA have higher rates of overall mortality than those with RSA). A decrease in RSA typically coincides with heart disease, such as congestive heart failure.

Heart rate variability (HRV) due to RSA has been generally thought to be simply a result (i.e., an indicator) of healthy autonomic function with no intrinsic value. A hypothesis is that HRV in and of itself is in some ways beneficial to health and survival. HRV may be antiarrhythmic as some studies have shown a decreased HRV precedes ventricular tachycardia. See Huikuri, et al. FREQUENCY DOMAIN MEASURES OF HEART RATE VARIABILITY BEFORE ONSET OF NON-SUSTAINED AND SUSTAINED VENTRICULAR TACHYCARDIA—Circulation Vol. 87, 1804, April 1993, pp. 1220–1228. A paper published recently in Circulation (Circ 1996;94:842–847) showed that RSA vs. fixed pacing rate improves pulmonary gas exchange and circulatory efficiency. However, until now pacemakers have ignored this phenomenon.

In the following description of the invention, it should be understood that rate responsive systems making use of the minute volume as a parameter first calculate a long term average for the minute volume of a patient and then determine the difference between this long term average and an instantaneous minute volume obtained as described below. The resulting differential parameter is referred to as "the minute volume" for the sake of brevity. However, in the drawings, the parameter is identified as dmv to indicate that, in fact, this parameter corresponds to the variation of the instantaneous minute volume from a long term average value.

OBJECTIVES AND SUMMARY OF THE INVENTION

In view of the above mentioned disadvantages of the prior art, it is an objective of the present invention to provide a pacemaker which dynamically responds to the instantaneous respiration and adjusts its pacing rate accordingly.

A further objective is to provide a metabolic rate responsive pacemaker which is capable of generating a metabolic indicated rate parameter adjustable with respiration to thereby adjust the pacing rate of a pacemaker in a manner which mimics accurately the sinus function.

Another objective is to provide a pacemaker which automatically tracks the activity level of the patient and modifies the pacing rate accordingly.

Other objectives and advantages of the invention shall become apparent from the following description. Briefly a pacemaker constructed in accordance with this invention includes a pacing generator generating pacing pulses in response to commands from a controller. The controller first establishes a base pacing rate preferably based on the metabolic demand of the patient. The pacemaker further includes a respiration sensor for detecting the patient's respiration. The base pacing rate is then adjusted in accordance to the respiration, in a manner similar to the respiration sinus arrhythmia in a healthy person.

Advantageously, minute volume is used by the metabolic demand parameter. Minute volume is derived from the transthoracic impedance which can be used to sense respiration.

Preferably, the pacemaker controller also monitors the physical activity of the patient. If the physical activity increases, the adjustment to the base rate is reduced. The adjustment of the base rate is also dependent on the age of the patient and by physical fitness level.

The adjustment may be either linear, in synchronism with the respiration or may be provided in discrete steps.

DETAILED DESCRIPTION OF THE INVENTION

Figure 1:
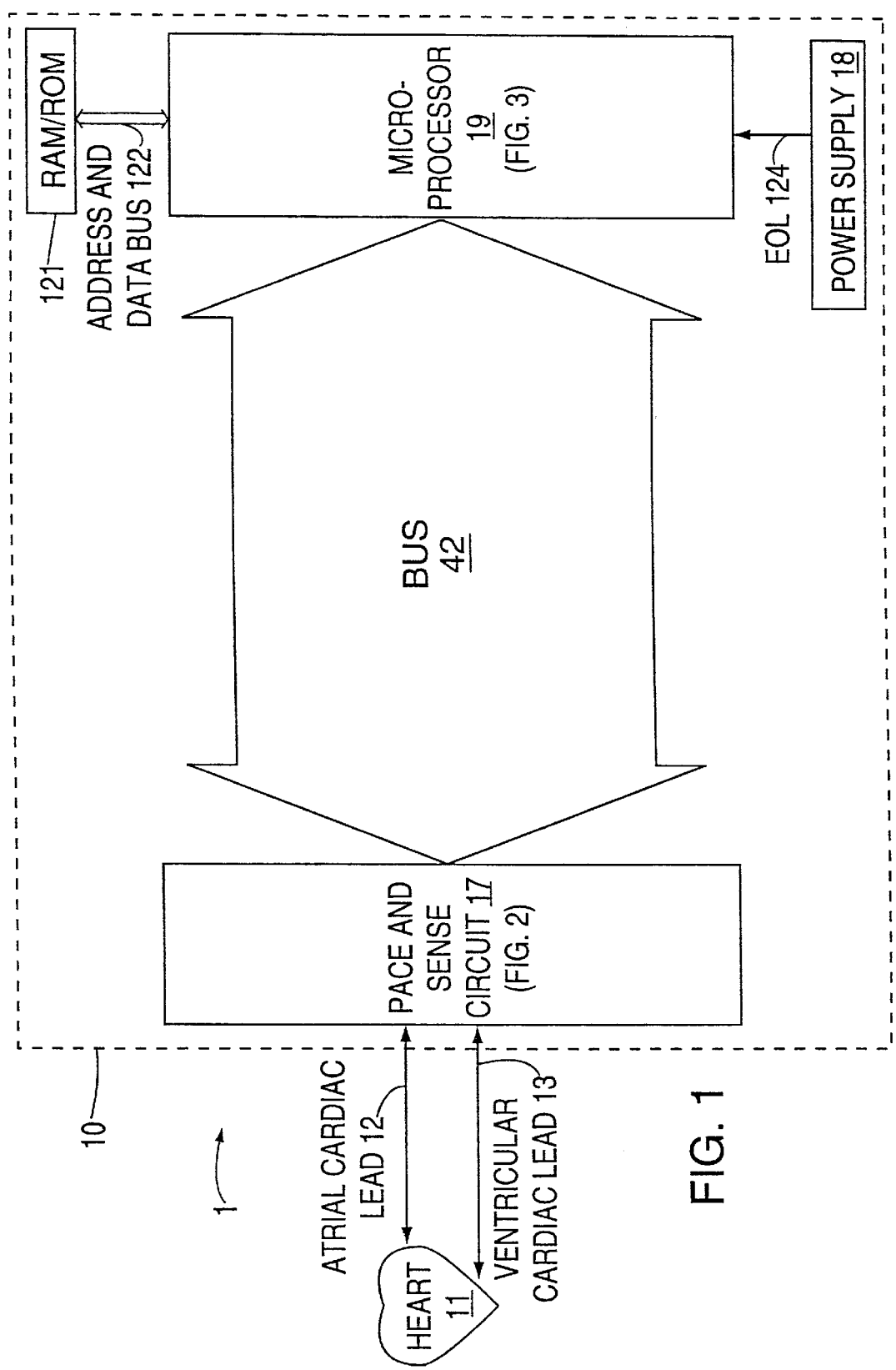
FIG. 1 shows a block diagram of a pacemaker constructed in accordance with this invention.

Details of a pacemaker 10 in accordance with the present invention are shown in FIGS. 1–8. FIG. 1 shows a block diagram of the pacemaker 10. The pacemaker 10 is designed to be implanted in a patient and is connected by leads 12 and 13 to a patient's heart 11 for sensing and pacing the heart 11 as described for example in U.S. Pat. No. 5,441,523 by T. Nappholz, entitled FORCED ATRIOVENTRICULAR SYNCHRONY DUAL CHAMBER PACEMAKER, and incorporated herein by reference. Briefly, the atrial cardiac lead 12 extends into the atrium of the heart 11 and the ventricular cardiac lead 13 extends into the ventricle of the heart 11. Leads 12 and 13 are used for both sensing electrical activity in the heart and for applying pacing pulses to the heart. The pacemaker 10 includes a pace and sense circuit 17 for the detection of analog signals from leads 12 and 13 and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides a voltage supply to the pace and sense circuit 17 and the microprocessor 19 by electrical conductors (not shown). The microprocessor 19 is connected to a random access memory/read only memory unit 121 by an address and data bus 122. A low power signal line 124 is used to provide to the microprocessor 19 a logic signal indicative of a low energy level of the power supply 18. The microprocessor 19 and the pace and sense circuit 17 are connected to each other by a number of data and control lines collectively shown in FIG. 1 as a bus 42.

Figure 2:
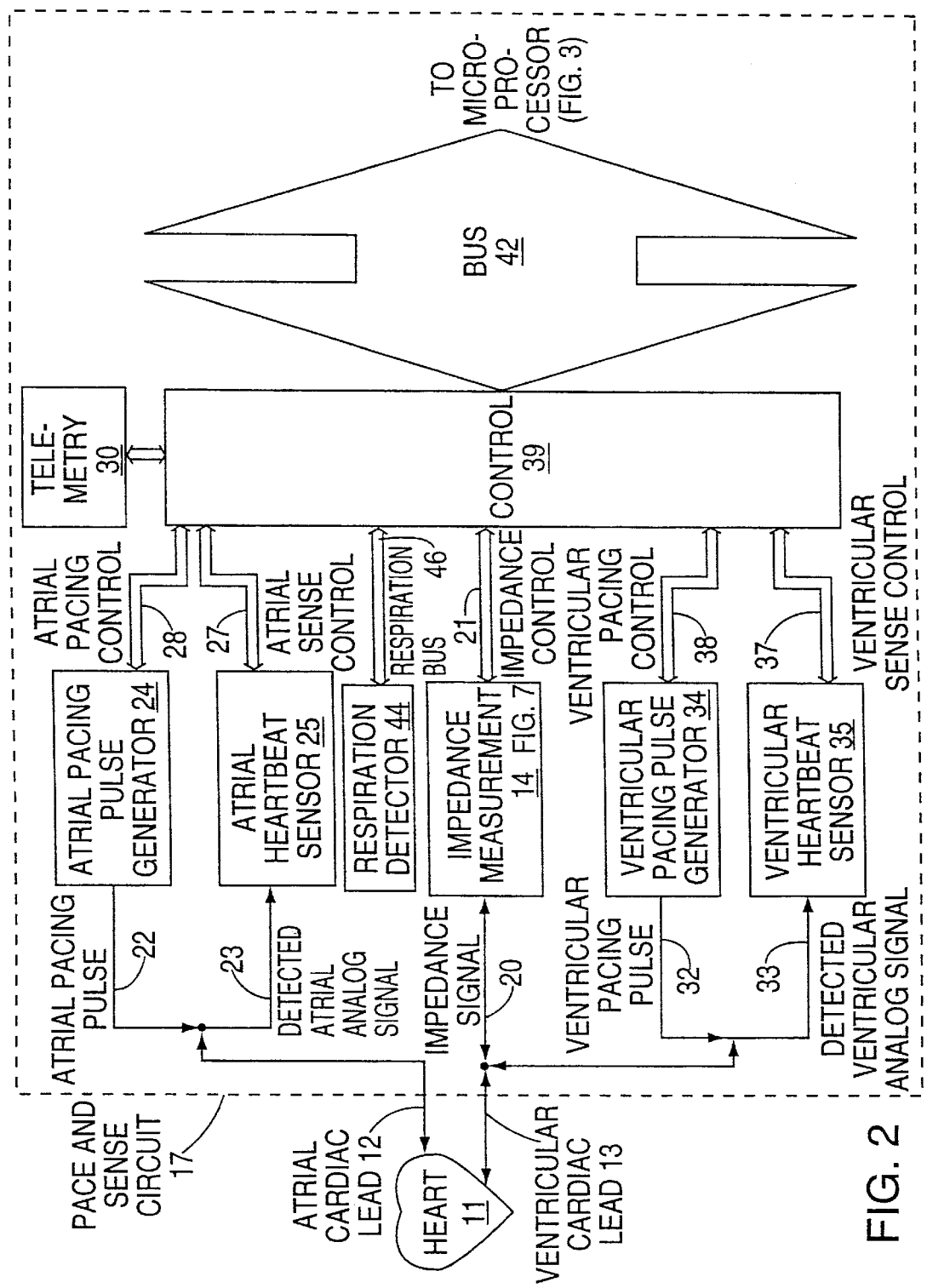
FIG. 2 shows a block diagram of the pace and sense circuit for the pacemaker of FIG. 1.

FIG. 2 shows details of the pace and sense circuit 17. The circuit 17 includes an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 also includes an impedance measurement circuit 14 for measuring a physiological parameter indicative of the patient's metabolic demand, and a respiration detector 44 for sensing the patient's respiration. The pace and sense circuit 17 also includes a control block 39 which is interfaced to the microprocessor 19.

In operation, the atrial and ventricular heartbeat sensor circuits 25 and 35 detect respective atrial and ventricular analog signals 23 and 33 from the heart 11 and convert the detected analog signals to digital signals. In addition, the heartbeat sensor circuits 25 and 35 receive an input atrial sense control signal on a control bus 27 and an input ventricular sense control signal on a control bus 37, respectively, from the control block 39.

The atrial pacing pulse generator circuit 24 receives from the control block 39, via an atrial pacing control bus 28, an atrial pace control signal and an atrial pacing energy control signal to generate an atrial pacing pulse 22 at appropriate times. Similarly, the ventricular pacing pulse generator circuit 34 receives from the control block 39, via a ventricular pacing control bus 38, a ventricular pace control signal and a ventricular pacing energy control signal to generate a ventricular pacing pulse 32. The atrial and ventricular pace control signals determine the respective timing of atrial and ventricular pacing that take place, while the atrial and ventricular pacing energy control inputs determine the respective magnitudes of the pulse energies.

The pacemaker 10 makes an impedance measurement when the microprocessor 19 sends a signal on the impedance control bus 21 to activate the impedance measurement circuit 14. The impedance measurement circuit 14 then applies a current to the ventricular cardiac lead 13 via lead 20 and measures a voltage resulting from the applied current, as discussed in more detail below. These current and voltage signals define an impedance characteristic of the patient's metabolic demand, and more particularly, of the instantaneous minute volume. This instantaneous minute volume is then filtered and further modified by subtracting from it a long term average value. The resulting parameter is the minute volume parameter. This minute volume parameter (dmv) is converted into a base pacing parameter, such as a metabolic indicated rate by the microprocessor.

The circuit 17 further includes respiration detector 44 used to detect the respiration function of the patient. This information is transmitted to the control block 39 via respiration bus 46. In the preferred embodiment of the invention, the respiration is determined from the impedance measurements taken by circuit 14 as discussed in detail below. If the metabolic demand is determined by other means, then the respiration detector 44 may use other external signals to detect respiration. The respiration signal is used to adjust the base pacing parameter to conform to respiration sinus arrhythmia, as discussed more fully below.

The telemetry circuit 30 provides a bidirectional link between the control block 39 of the pace and sense circuit 17 and an external device such as a programmer. It allows data such as the operating parameters to be read from or altered in the implanted pacemaker.

Figure 3:
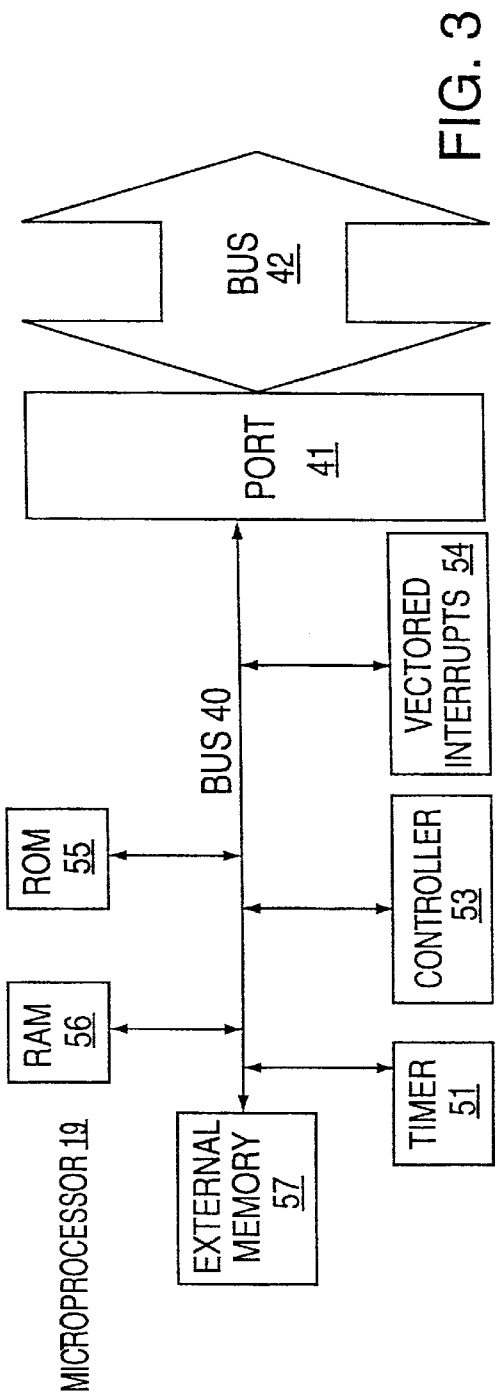
FIG. 3 shows a block diagram of a microprocessor for the pacemaker of FIG. 2.

FIG. 3 shows the microprocessor 19 having a timer circuit 51 for generating several timing signals, a controller 53, a vectored interrupts circuit 54, a ROM 55, a RAM 56, an external memory 57 and an interface port 41. Signals between these elements are exchanged via an internal communications bus 40. The RAM 56 acts as a scratchpad and active memory during execution of the programs stored in the ROM 55 and used by the microprocessor 19. ROM 55 is used to store programs including system supervisory programs, detection algorithms for detecting and confirming arrhythmia, and programming for determining the rate of the pacer, as well as storage programs for storing, in external memory 57, data concerning the functioning of the pulse generator 10. The timer circuit 51, and its associated control software, implements some timing functions required by the microprocessor 19 without resorting entirely to software, thus reducing computational loads on, and power dissipation by, the controller 53.

Signals received from the telemetry circuit 30 permit an external programmer (not shown) to change the operating parameters of the pace and sense circuit 17 by supplying appropriate signals to the control block 39. The communication bus 42 serves to provide signals indicative of such control to the microprocessor 19.

The microprocessor 19 through its port 41 receives status and/or control inputs from the pace and sense circuit 17, including the sense signals from the sensors 25, 35 (FIG. 2). Using controller 53, it performs various operations, including arrhythmia detection, and produces outputs, such as the atrial pace control and ventricular pacing control, which determine the type of pacing that is to take place. The rate of the atrial and/or ventricle pacing is adjusted by controller 53 not only to conform to the metabolic demand of the patient but also in accordance with the respiration of the patient, as set forth below.

The pacemaker 10 of the present invention functions properly using any metabolic indicator rate system, so long as that system is able to reliably relate the sensed parameter to an appropriate matching of metabolic demand with the paced rate. However, the preferred embodiment of the invention employs the impedance measurement circuit 14, shown in FIG. 5, which measures the thoracic impedance to determine the respiratory minute volume as described generally in U.S. Pat. No. 4,901,725, incorporated herein by reference.

Figure 4:
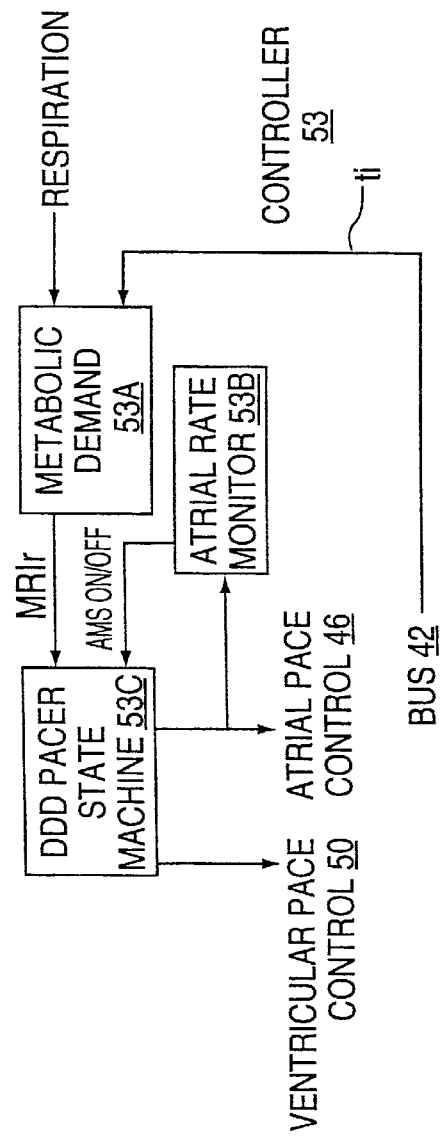
FIG. 4 shows details of the controller for the microprocessor of FIG. 3.

FIG. 4 shows the block diagram of the controller 53 of FIG. 3. The controller 53 includes a pacer 53C, which is preferably a state machine, a metabolic demand detector 53A and an atrial rate monitor 53B. The metabolic demand detector 53A uses the data supplied via the internal bus 40 and the bus 42 from the impedance measurement circuit 14 and the respiration detector 44 to relate the minute volume indicated by the impedance measurement and the respiration to the Metabolic Rate Interval (MRIr). This interval is then used by the state machine 53C to determine the length of each interval in the timing cycle. In response, the state machine 53C generates on demand control signals for generating atrial and/or ventricular pacing pulses. While the pacemaker 10 is preferably operating in a DDDR mode, it should be understood that it can operate in other modes as well. The atrial rate monitor 53B generates an Automatic Mode Switching (AMS) signal upon detection of a non-physiological atrial rate and rhythm. This AMS signal automatically switches the pacemaker 10 to a ventricular pacing mode, where atrial pacing is temporarily disabled. When a physiological atrial rate resumes, the AMS signal is deactivated and the pacemaker returns to an atrial tracking mode. Except for the adjustment in the MRI due to the respiration the operation described so far is known from U.S. Pat. No. 5,441,523, incorporated herein by reference.

The respiration of a patient may be detected using various methods. In commonly assigned co-pending application Ser. No. 08/641,223, filed Apr. 30, 1996, now U.S. Pat. No. 5,792,196, entitled RATE-RESPONSIVE PACEMAKER WITH RAPID VOLUME DETERMINATION, incorporated herein by reference, the metabolic demand parameter is minute volume which is determined by measuring variations in the transthoracic impedance of the patient and detecting the zero-crossings of this parameter. The present inventor has realized that the variations in this parameter correspond to the respiration of the patient and hence the separate instantaneous respiratory phases of inspiration and expiration could be detected and dynamically adjust the metabolic indicated pacing interval MRI.

Figure 7:
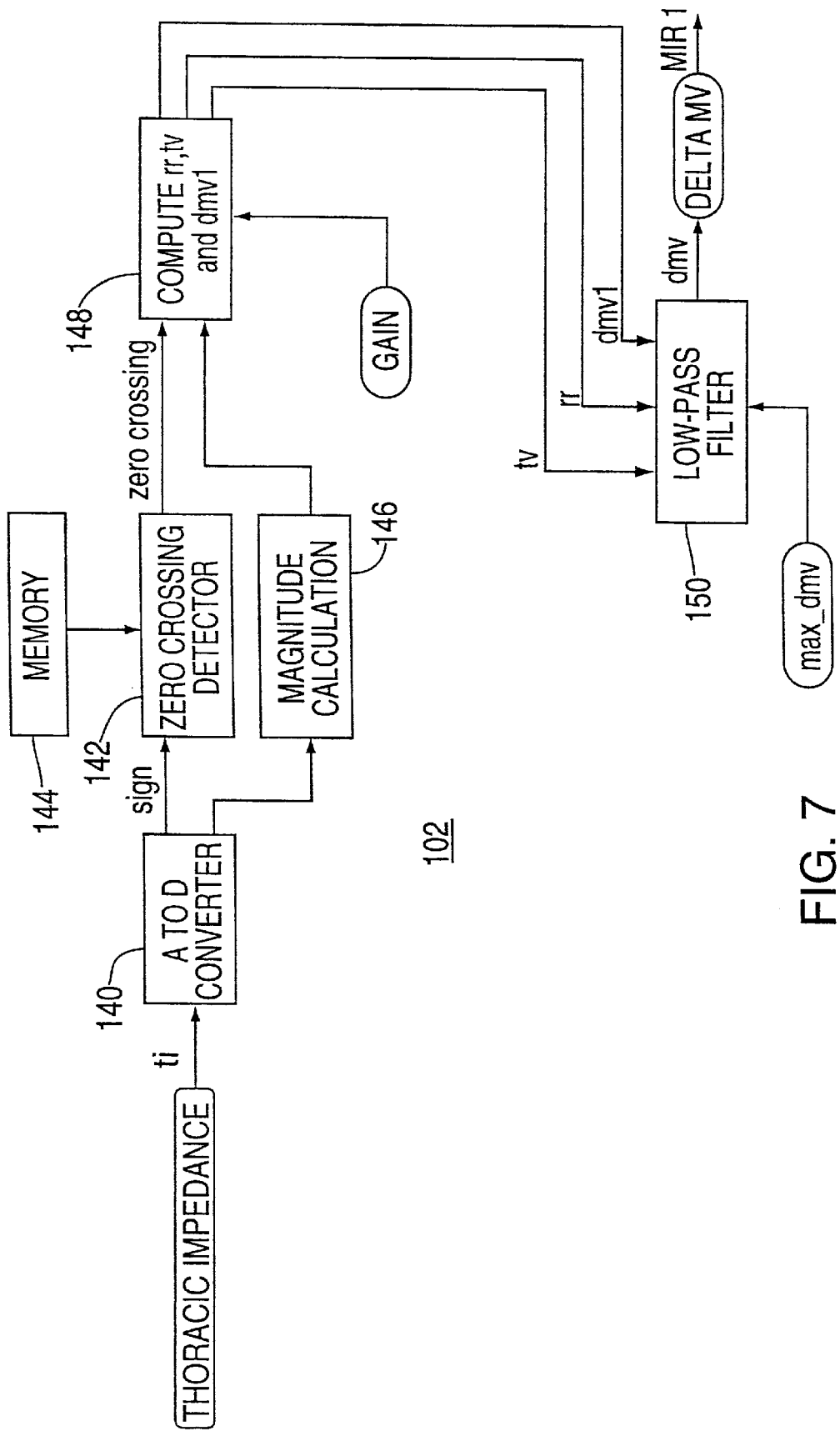
FIG. 7 shows a prior art block diagram of zero crossing detection circuit used to convert thoracic impedance into a metabolic rate interval.

As disclosed in the above-mentioned application Ser. No. 641,223, and shown in FIG. 5, impedance measurement circuit 14 is coupled by connection 20 to one or more of the patient's leads, such as lead 13. The circuit 14 generates a time-dependent signal ti indicative of the sensed thoracic impedance of the patient. The signal is fed to a delta minute ventilation (dmv) generator 102 which converts this ti signal into a corresponding dmv signal as shown in FIG. 7 and discussed in more detail below. The signal dmv is fed to a circuit 104 which uses a conformal mapping (discussed in more detail below) to generate a corresponding metabolic indicated rate MIR1.

Signal MIR1 is fed to a paced pulse interval calculation circuit 108. The interval MRIr calculated by circuit 108 is used by the state machine 53 (FIG. 4) to calculate the pacing intervals as discussed above. In the present invention, circuit 53C is modified to take the instantaneous respiration into account as discussed below in relation to FIG. 8.

The thoracic impedance ti is also fed to a respirator detector 100. The respiration detector 100 detects the instantaneous respiration of the patient and based on this, and other factors derives a correction coefficient SC.

Figure 6:
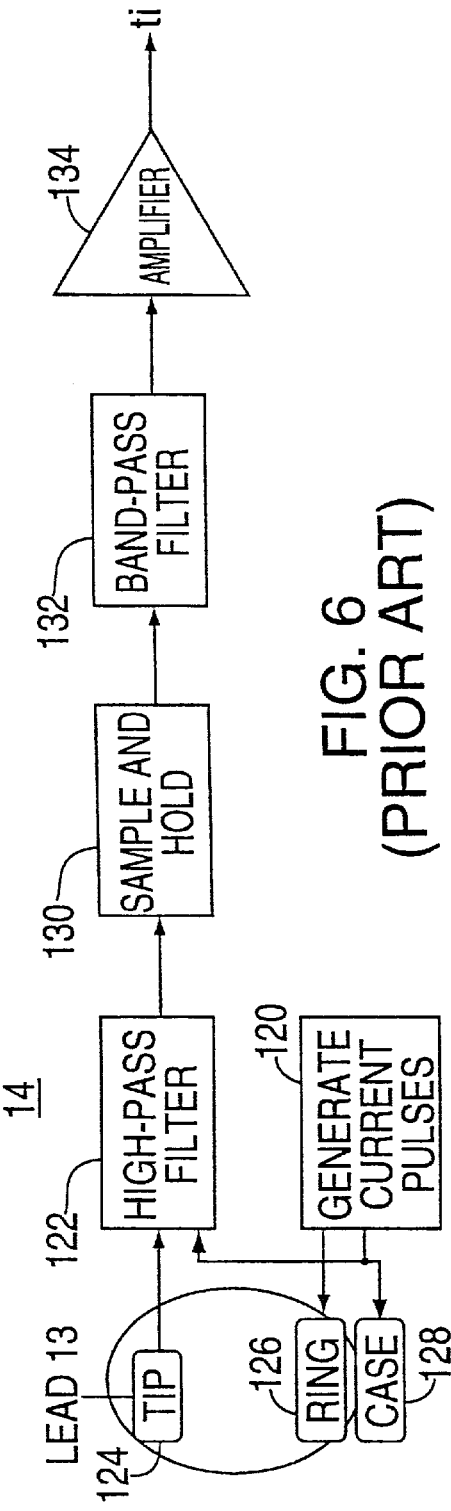
FIG. 6 shows a block diagram for a prior art circuit used to determine thoracic impedance.

Referring now to FIG. 6, a known thoracic impedance sensor 100 includes a current generator 120 and a high pass filter 122 coupled to one of the patient leads, such as lead 13. (It should be clear that other leads may be used as well for determining the dmv parameter as described, for example, in U.S. Pat. No. 5,562,712). The lead 13 includes a tip electrode 124 and a ring electrode 126. As known in the art, at predetermined times, the current generator 120 applies current pulses between the ring electrode 126 and pacemaker case 128, and the corresponding voltage is sensed between the tip electrode 124 and case 128. Typically, each current pulse has a pulse width of about 7.5 $\mu$sec, at repetition rate of about 18 pulses per second and an amplitude of about 1 mA. This pulse repetition rate is chosen at well above twice the Nyquist sampling rate for the highest expected intrinsic heart beats, and in the present invention it is preferable so that respiration can be easily differentiable from cardiac impedance signals.

The sensed voltage, is passed through the high pass filter 122 selected to accept the 7.5 $\mu$sec pulses and exclude all noise signals. After filtering, the voltage signal is sampled by a sample and hold (S/H) circuit 130. Preferably the S/H circuit takes samples before the start of the test pulses from generator 120 (to enhance the effectiveness of the filter 122) as well as toward the end of the pulse duration.

The output of circuit 130 is passed through a band pass filter 132 which selects the signals in the range of normal respiration rate, which is typically in the range of 5–60 cycles/minute.

The output of the BPF 132 amplified by amplifier 134 to thereby generate the thoracic impedance signal ti. The amplifier raises the signal ti to a level sufficient so that it can be sensed and processed by the delta minute volume generator 102.

Referring to FIG. 7, circuit 102 includes an A/D converter 140, a zero crossing detector 142, a magnitude calculator circuit 146, calculator circuit 148 for calculating parameters rr, tv and dmv, and a low pass filter 150. Circuits 140 and 142 are preferably discrete hardware components while the remaining circuits 146, 148, 150 are implemented by a microprocessor, however are shown here as discrete circuits for the sake of clarity.

Within circuit 102, the thoracic impedance signal ti is first fed to an A/D converter 140 to generate a digital representation of the signal ti. This converter generates two outputs; a sign signal indicating the polarity of the signal ti and a magnitude output indicating the amplitude of ti. This magnitude is of course the same as the absolute value of the signal ti. The magnitude is sent to magnitude calculator circuit 146.

The sign signal is fed to a zero crossing detector 142 which generates a zero crossing indicating output whenever it detects a sign change of signal ti. Associated with detector 142 is a memory 144 for storing the polarities of the last N samples from converter 140. N may be for example 15.

Preferably the zero crossing detector 142 is implemented so that it adapts to changes in the heart rate. This feature was found to improve the rejection of cardiac stroke volume artefact and other noise sources. More specifically, the zero crossing circuit detector 142 detects a zero crossing each time more than m of n successive samples have a sign opposite to the sign value which was detected at a previous zero crossing. The values m and n are adjusted according to the paced or sensed pulse rate. This insures that the zero crossing cannot be detected at the present heart rate, but can be detected at lower rates. This feature is especially beneficial for pediatric patients who have a much higher respiration rate than older patients. These higher rates can be tracked more efficiently by the present zero crossing detector 142.

The magnitude from circuit 146 and the zero crossings are fed to compute circuit 148.

As part of its operation compute circuit 148 calculates the parameters rr (respiration rate), tv (tidal volume) and dmv1. These parameters rr, tv and dmv1 are updated every 1.5 seconds if a corresponding zero crossing is detected. If no zero crossings are detected for up to 12 seconds, the values of these parameters are left unchanged. After 12 seconds without zero crossings, the values are gradually reduced toward the baseline parameter, to prevent inappropriate high rate pacing.

The following relationships approximate the relationships between heart rate hr (in BPM), tidal volume tv (in liters), and delta minute ventilation dmv (in liters per minute), based on patients having average heights and weights:

dmv=(hr−min_hr)/1.5 and tv=dmv/rr where min_hr is the heart rate at rest and rr is the respiration rate in breaths per minute and is determined from the zero-crossings.

Getting back to FIG. 7, after the parameters rr, tv and dmv1 are computed delta minute ventilation dmv1 is passed through the low-pass filter 150 to smooth the results. Preferably the filter 150 is a single pole low-pass filter, which has been found to model physiological response more closely than more complex filters. The filter is implemented preferably digitally. In a fixed-point arithmetic implementation an accumulator (incorporated in filter 150, not shown) must have more bits of precision than the delta minute ventilation values. The accumulator range is limited to prevent the filter from exhibiting delayed response following very high or very low input values.

Figure 5:
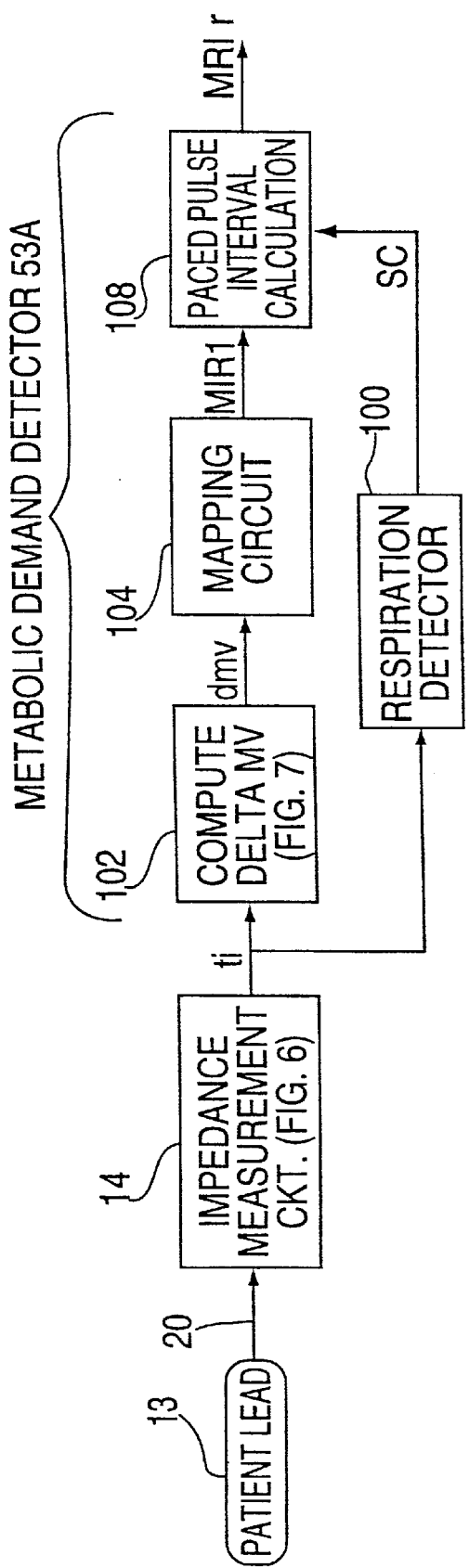
FIG. 5 shows details of the metabolic demand detector for the controller of FIG. 4.

The circuitry of FIG. 5 is discussed in more detail in application Ser. No. 08/641,223 filed Apr. 30, 1996, incorporated herein by reference.

The output then of filter 150 is the delta minute volume parameter dmv in FIG. 5. Next, this parameter dmv must be converted into a metabolic indicated rate (MIR) parameter. Schemes for performing this function are well known in the art. One such scheme is disclosed in copending application Ser. No. 08/641,223 filed Apr. 30, 1996, entitled RATE RESPONSIVE PACEMAKER WITH AUTOMATIC RATE RESPONSE FACTOR SELECTION now U.S. Pat. No. 5,792,196, incorporated herein by reference. As disclosed in this reference, a curvilinear mapping between minute ventilation and MIR is preferable because it can be modeled after physiological data on a wide range of normal subjects.

Figure 8:
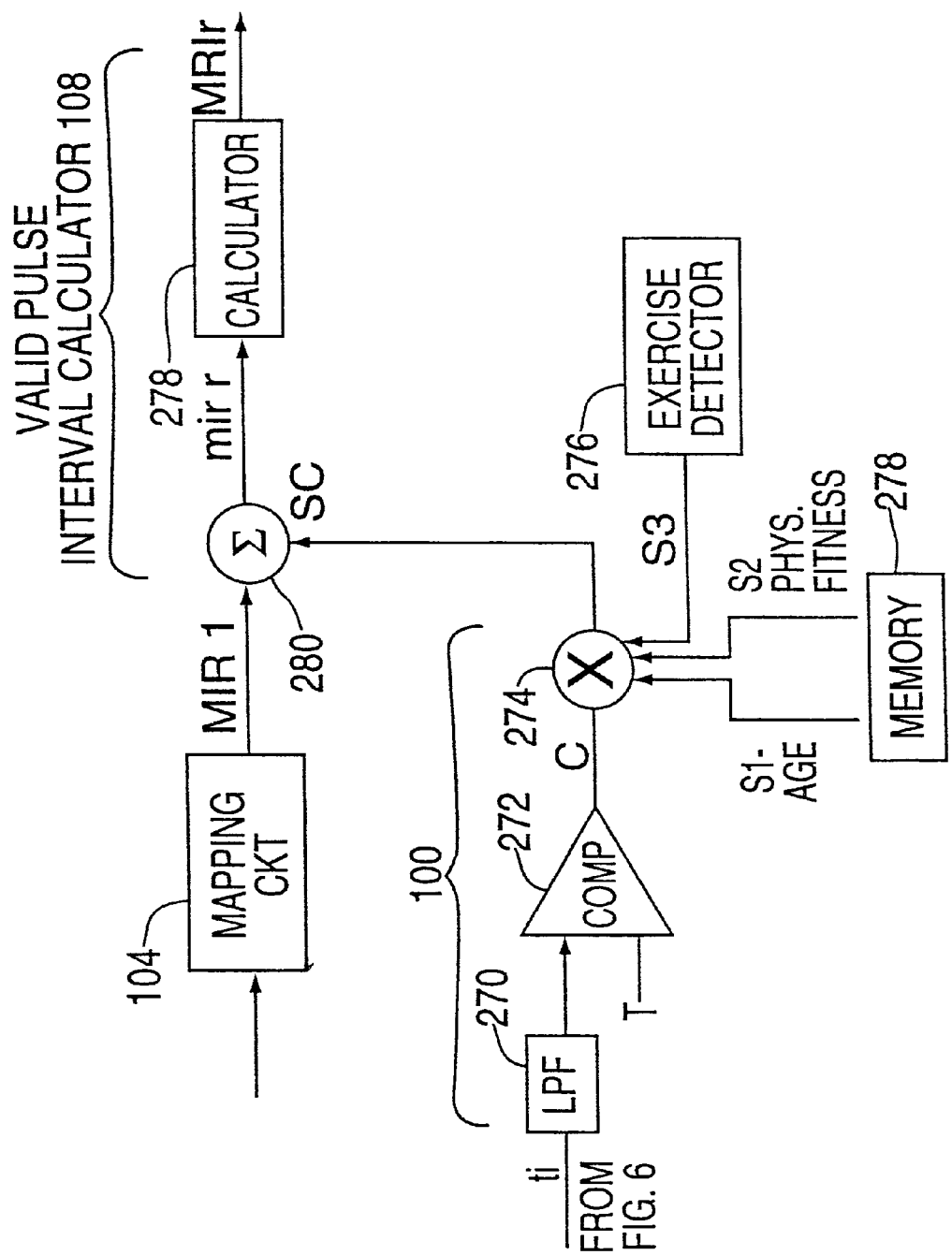
FIG. 8 shows details of the circuitry used to convert the thoracic impedance into a respiration signal, and details of adjusting the metabolic indicate rate in accordance with the respiration.
Figure 9:
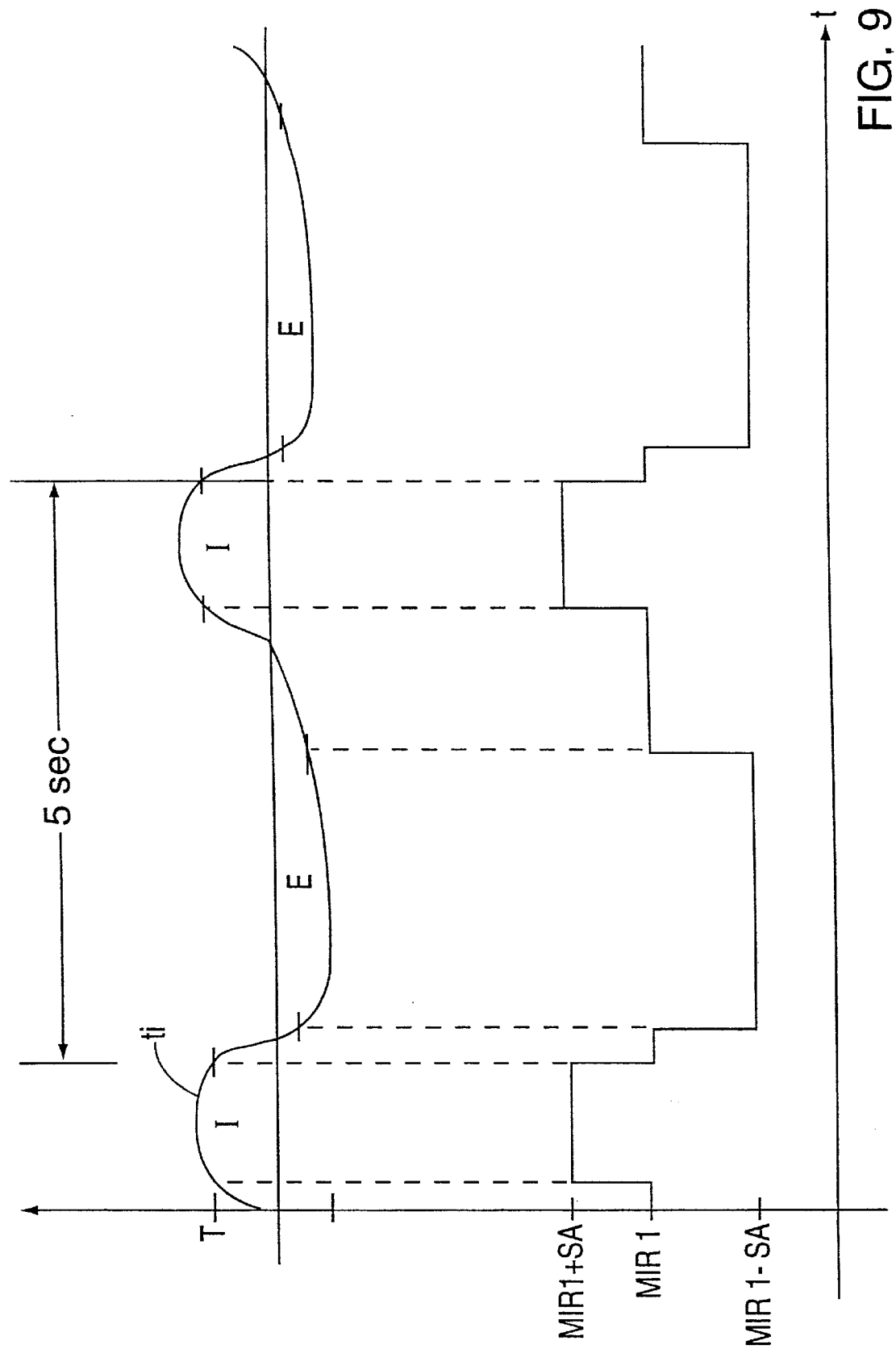
FIG. 9 shows a graph of a typical respiration cycle and the corresponding value of the respiratory factor.

Referring now to FIG. 8, the respiration is derived and used in the present invention as follows. The transthoracic impedance signal ti from amplifier 134 (FIG. 6) is fed into a low pass filter 270. The output of this filter is fed to a comparator 272. This comparator 272 determines if the absolute value of signal ti (after filtering) is outside a preselected range. Typically, as shown in FIG. 9, the signal ti is essentially a sinusoidal signal with a period of about five seconds. The portion above the horizontal axis corresponds to inspiration and the portion below the horizontal axis corresponds to expiration. (The two respiration phases may have different durations, however this effect has been omitted for the sake of simplicity.) The comparator 272 also receives the threshold T as an input. This threshold may be a programmable parameter. The comparator then produces an output C which has the following values, as indicated in FIG. 9:

C=A if ti>T

C=0 If −T<ti<T;

C=−A if ti<−T.

The output C of comparator 272 is fed to a multiplier 274. The multiplier is used to scale by one or more of the scaling constants S1, S2, S3. Scaling constants S1 and S2 are indicative of the patient's age and physical fitness. These parameters may be stored by the physician into memory 278. Scaling constant S3 is derived from an exercise detector 276. This detector may monitor the intrinsic beat of the heart and/or the metabolic demand (dmv) for increases. Other exercise detectors are known in the art as well. Each of these scaling factors tend to affect the respiratory sinus arrhythmia. More specifically RSA decreases with age, increases with improved fitness, and decreases during exercise.

As seen in FIG. 8, the parameter mir1 from mapping circuit 104 is fed to a summer 280. The summer 280 also receives the output SC of multiplier 274, and it generates a parameter mirr defined by:

mirr=mir1+SC.

Since SC could be either zero positive or negative, the parameter mirr could be higher or lower than mir1. (In other words, SC may have an absolute value of either 0 or about 3–15 ppm). For example, mirr may range between mir1−10 and mir+10 ppm.

The parameter mirr is fed to calculator 278. This calculator 278 converts mirr into a corresponding metabolic rate responsive interval signal MRIr.

The parameter MIR1 is then used to generate the metabolic indicated rate interval (MRI) by calculator 108. The paced pulse interval is inversely related to the paced heart rate as indicated by the following equation.

ppi=60000/phr ppi=paced pulse interval, milliseconds phr=paced heart rate, pulses per second Other time intervals of the pacing cycle are computed by the state machine 53C (FIG. 4) using the paced pulse interval and/or the heart rate.

Signal MIRr is then fed to state machine 53C. The result of this modified signal is that during inspiration, the pacing rate is increased by about 3–15 ppm while during expiration, the pacing rate decreases by about the same amount. As discussed above, this swing or respiration component is dependent on the age, physical fitness and current activity level of the patient.

As shown in FIG. 9, the respiration signal ti is in effect quantized to three levels (mir1+SC, mir1, mir1−SC) and the corresponding MIRr can also have one of three values depending upon the phase of respiration.

Figure 10:
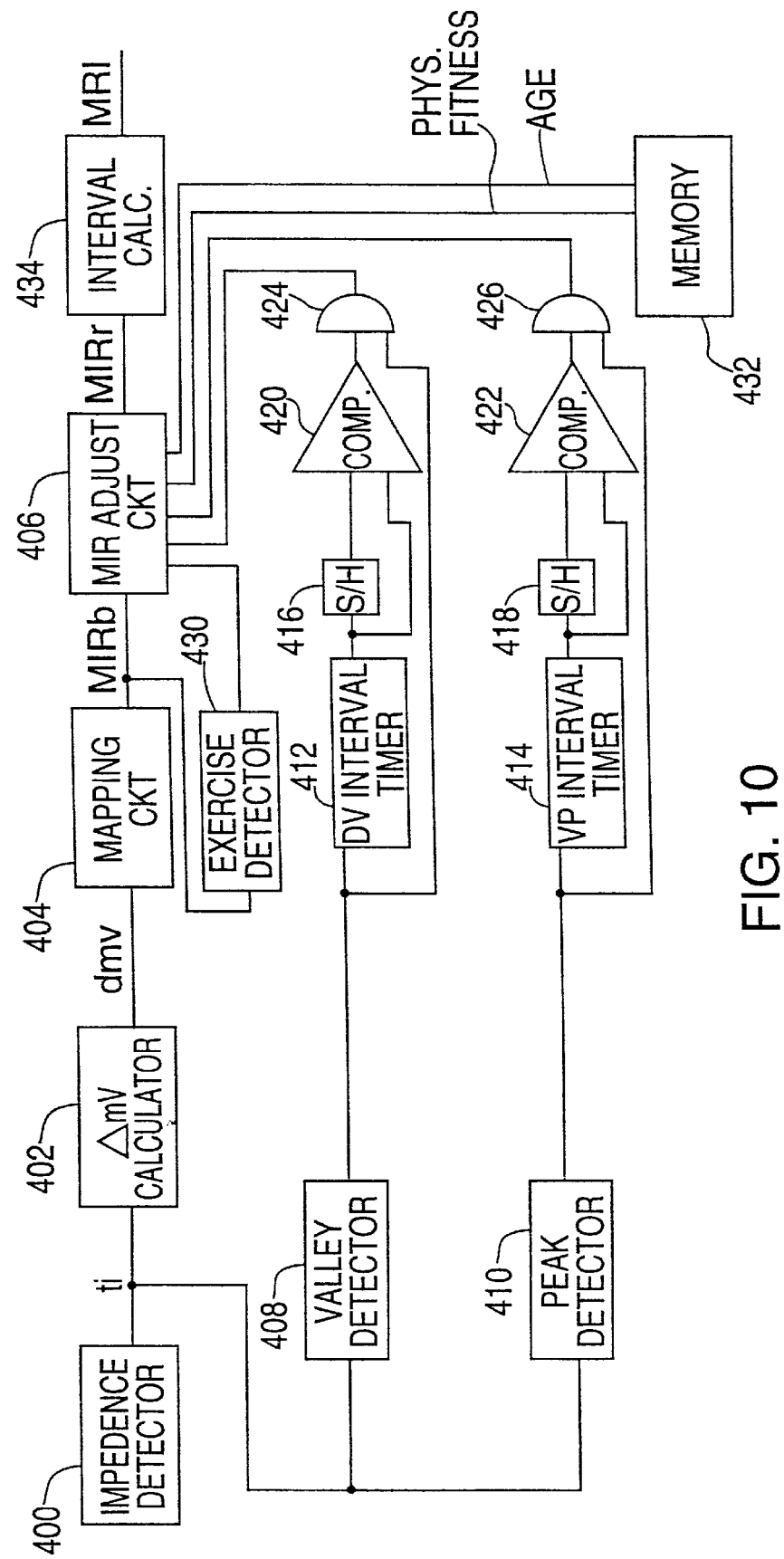
FIG. 10 shows an alternate circuit for adjusting a base parameter using the respirator signal.
Figure 11:
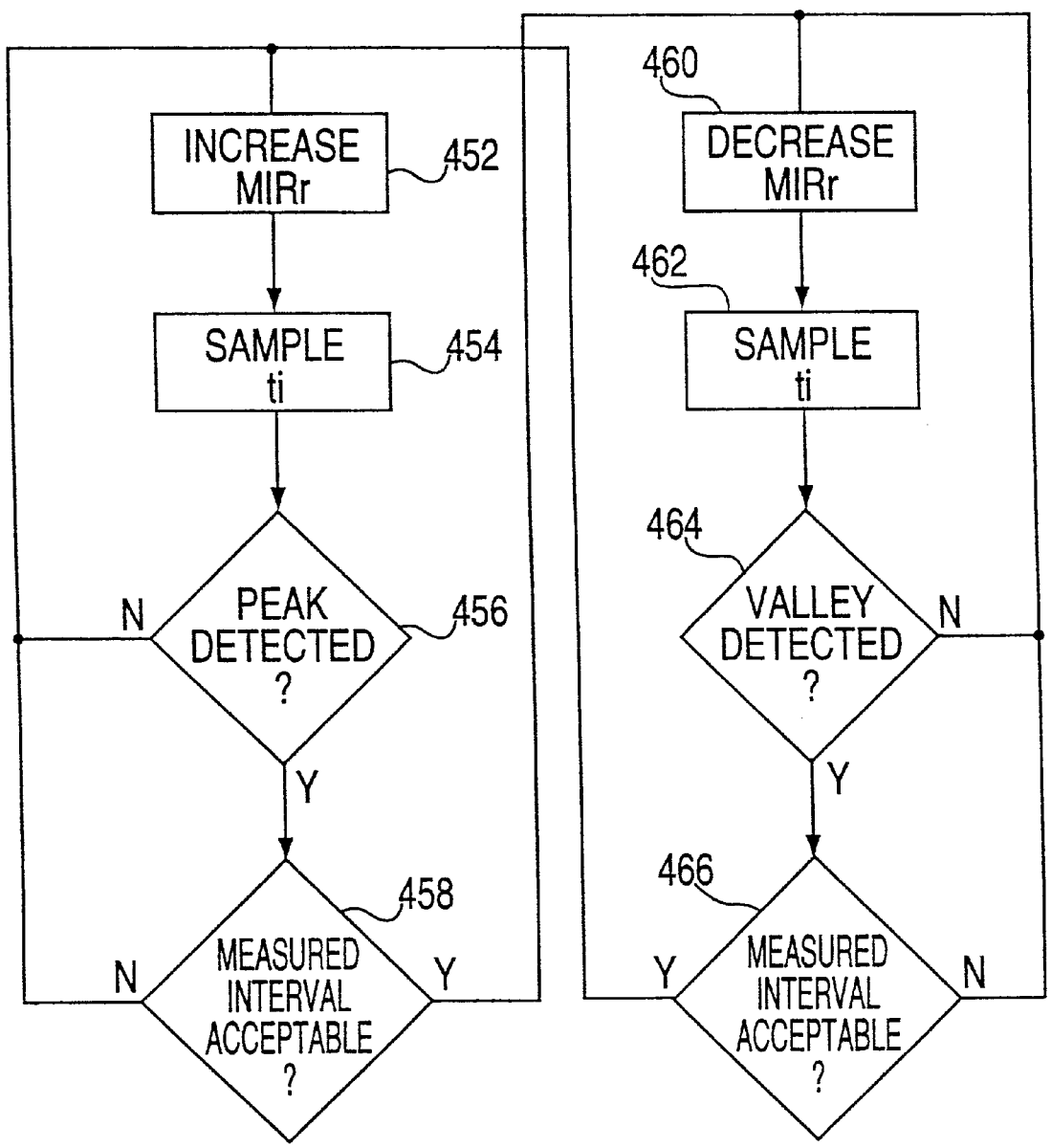
FIG. 11 shows a flow chart for the operation of the circuit of FIG. 10.

A more generic embodiment of the invention is shown in FIGS. 10 and 11, in which the respiration rate is not directly quantized and the parameter MRIr is varied continuously between a maximum and a minimum level. In this embodiment, an impedance determinator 400 determines a respiration indicative parameter such as the instantaneous transthoracic impedance ti and feeds the same to a differential dmv calculator 402. This calculator converts the parameter ti into a differential dmv parameter which is fed to a mapping circuit 404. The mapping circuit then generates a baseline metabolic indicated rate parameter MIRb. This parameter is then fed to an MIR adjusting circuit 406. It should understood that for the purposes of this invention, other means of determining the respiration may be used, in which case, the baseline MIRb may be derived from other parameters as discussed above.

Figure 12:
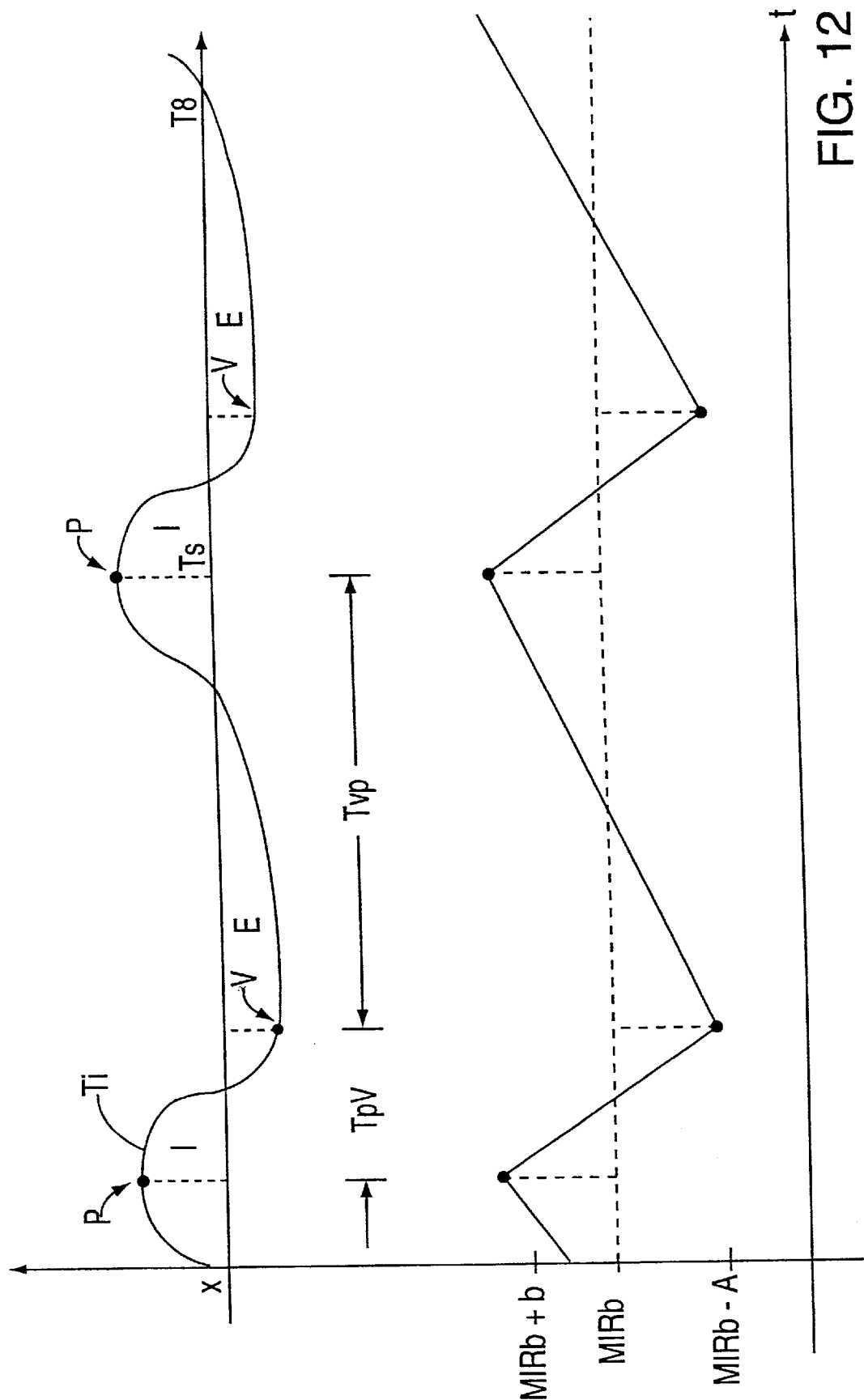
FIG. 12 shows a graph of respiration signal and a corresponding adjusted pacing rate as determined by the circuit of FIG. 10.

As seen in FIG. 12, the respiration or transthoracic impedance curve ti is characterized by a positive lobe (I) for the inspiration and a negative lobe (E) for the expiration. Generally the two lobes I and E are not identical and moreover, each lobe is asymetrical. The interval Tpv between a peak P and the succeeding valley V is generally much shorter than the interval Tvp between successive valleys and peaks, as shown.

Referring now to FIG. 10, the parameter ti is fed to a valley detector 408 and a peak detector 410. These detectors are used to detect the valleys V and peaks P of ti. Two interval timers 412, 414 each receive an output from detectors 408, 410. Timer 412 is used to determine the interval Tpv while timer 414 is used to determine interval Tvp.

The output of each timer 412, 414 is fed to a corresponding sample-and-hold (S/H) circuit 416, 418. The S/H circuits may hold the previous interval, or preferably a running average of the last several previous intervals. The output of each S/H circuit is fed to a comparator 420, 422. Comparators 420, 422 compare the current interval (Tvp, Tpv), with the corresponding values from the S/H circuits 416, 418.

The outputs of comparators 420, 422 are fed to AND gates 424, 426. The AND gates also receive a corresponding input from detectors 408, 410, as shown. The outputs of the AND gates are fed to MIR ADJUST circuit 406 as discussed below.

The parameter MIRb is fed to an exercise detector 430. This detector 430 determines from the value of MIRb the onset and offset of exercise. The detector 422 controls the maximum amplitude of adjustment performed by adjustment circuit 406.

The operation of the circuit of FIG. 10 is now described in conjunction with the flow chart of FIG. 11. Initially, i.e., at t=0, ti starts a positive sinusoidal swing toward its maximum value at P. The value of ti is sampled at about 18 Hz. Therefore at t=0, the MIRr is increased by an incremental amount in step 452 (FIG. 11). The first sample after t=0 is detected in step 454. In step 456 peak detector 410 looks for a peak. For example, the peak detector may look for three consecutive values $ti_{1,2,3}$ which are smaller than the value of a previous sample $ti_0$. At 18 Hz sampling rate, this approach results in a response time of about 200 msec.

If no peak is detected in step 456, then the parameter MIRr is increased again in step 452 and the next sample of ti is taken. This process continues until step 456 detects a peak.

Getting back to FIG. 10, when a peak P is detected, the output of the interval timer 414 is compared to previous intervals Tvp by comparator 422, as previously described. (In the example given, the evaluation of MIRr has already started for several cycles prior to t=0 and hence the S/H circuits 416, 418 hold values of Tpv, Tvp based on these early cycles). If a peak is detected by detector 410, then the output of the interval timer 414 is compared to the interval stored in the S/H circuits 416, 418 to determine if the interval measured by timer 412 is acceptable (i.e. within e% of the value in S/H 418) (step 456)). If it is not, then the detected Tvp peak is assumed to be noise and is ignored. If the interval is acceptable, then in step 460 the parameter MIRr is decreased by the same incremental amount as in step 452. Steps 462, 464 and 466 follow the same logic as steps 454, 456, 458 for decreasing MIRr. The result, as shown in FIG. 12 is that the parameter MIRr increases or decreases linearly in synchronism with the respiration parameter ti. More particularly, MIRr swings linearly between the limits MIRb−A<MIRr<MIRb+A.

Preferably, A is in the range of 3–15 ppm.

It has been found that the variability of the intrinsic heart rate decreases with the intensity of exercise so that it virtually diminishes as the heart rate becomes greater than 100 bpm. This can be implemented in two ways by the circuit of FIG. 10. The simplest way is to monitor the baseline metabolic parameter MIRb. If MIRb is below 100 ppm, A is 15 ppm, assuming all other factors are constant. If MIRb is 100 or above, A=0. Thus in this case exercise detector 430 may be a simple comparator.

However, in healthy patients, the heart rate variability normally changes gradually and is not discontinuous. This behavior may be simulated by generating an exercise indicia EI by detector 422 and feed this indicia to the adjustment circuit. Preferably this indicia, is used to change MIRr gradually between preselected ranges of MIRb. For example, the indicia EI may be (MIRb−50)/50, in which case the parameter A for MIRr can be expressed as:

A=15(1−EI) for 50<MIRb<100 ppm and

For MIRb>100 ppm, A=0.

In addition, the value of A may be adjusted downward for age or physical fitness. Therefore the age and/or physical fitness of the patient may be stored in a memory 432 by the clinician.

The parameter MIRr is fed to interval calculator 434 which then calculates a corresponding paced pulse interval MRIr.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. A rate responsive implantable pacemaker comprising:
   a sensor for sensing intrinsic activity in a patient's heart and generating a sensed signal;

a pace generator generating pacing signals on demand in response to pacing commands;

a metabolic demand detector detecting a metabolic demand of said patient and generating a metabolic demand parameter;

a respiration detector detecting a respiration of said patient and generating a respiration parameter;

an adjuster circuit receiving said metabolic parameter and said respiration parameter and adjusting said metabolic parameter cyclically in accordance with said respiration parameter to generate an adjusted metabolic parameter which follows said respiration; and a controller receiving said sensed signal and said adjusted metabolic parameter to generate said command, whereby said pace generator generates said paces dependent on the patient's respiration.

2. The pacemaker of claim 1 wherein said metabolic demand detector detects minute volume as said metabolic demand parameter.

3. The pacemaker of claim 2 wherein said respiration detector is coupled to said metabolic demand detector and is arranged to generate said respiration parameter based on said minute volume.

4. The pacemaker of claim 1 wherein adjusting circuit includes adding and subtracting means which adjust said metabolic parameter by cyclically adding and subtracting a constant value from said metabolic parameter, in accordance with said respiration parameter.

5. The pacemaker of claim 1 wherein said adjusting circuit includes means for varying said adjusted metabolic parameter linearly between a baseline and one of a maximum value and a minimum value.

6. The pacemaker of claim 5 wherein said means for varying said adjusted metabolic parameter is adapted to use said metabolic parameter as said base line.

7. The pacemaker of claim 5 wherein said adjusting means is further adapted to adjust said adjusted metabolic parameter based on one of said patient's exercise level, age and fitness level.

8. The pacemaker of claim 7 further comprising an exercise level detector for detecting said exercise level.

9. The pacemaker of claim 7 further comprising a memory for storing the patient's age and fitness level.

10. An implantable pacemaker comprising:

a cardiac sensor that senses intrinsic cardiac activity in a patient's heart and generating sensed signals;

a pacing generator that generates pacing pulses in response to commands;

a respiration sensor that senses a respiration of said patient and generates corresponding respiration signals; and a controller receiving said sensed and respiration signals and generating in response said commands;

wherein said controller generates said commands for pacing said heart at a base pacing parameter, said pacemaker further comprising a rate adjusting circuit that adjusts said commands cyclically in accordance with said respiration signal to pace said heart at an adjusted rate from said base rate, said adjusted rate following said respiration signal.

11. The pacemaker of claim 10 wherein during a period between increasing and decreasing said base rate, said adjusting circuit is arranged to maintain said base rate unchanged.

12. The pacemaker of claim 10 wherein said adjusting circuit includes means that adjusts said adjusted rate gradually between an upper limit and a lower limit.

13. The pacemaker of claim 12 wherein said respiration signal includes peaks alternating with valleys, said peaks and valleys defining inspiration and expiration periods for said respiration and wherein said upper and lower limits of said adjusted rate substantially coincide with said peaks and valleys respectively.

14. The pacemaker of claim 10 wherein said adjusting circuit adjusts said adjusted rate by adding and subtracting a level A to and from said base rate.

15. The pacemaker of claim 14 further comprising an exercise detector for detecting an exercise period of said patient, said level A being dependent on said exercise period.

16. The pacemaker of claim 15 wherein said level A decreases in the presence of exercise.

17. The pacemaker of claim 15 wherein said level A decreases when said patient exceeds a preselected exercise level.

18. The pacemaker of claim 16 wherein said level A is decreased linearly from a first value to a second value as the pacing rate increases between a first heart rate and a second heart rate due to exercise.

19. The pacemaker of claim 18 wherein said adjusting circuit ceases adjusting the base rate when said heart rate increases above a preselected threshold.

20. The pacemaker of claim 16 wherein said level A decreases from a first amplitude to a second amplitude when the patient's exercise level increases above a preselected threshold.

21. The pacemaker of claim 10 wherein said respiration detector includes a transthoracic impedance sensor for sensing a transthoracic impedance of said patient, said transthoracic impedance being dependent on said respiration.

22. The pacemaker of claim 10 further comprising a metabolic detector for detecting a metabolic demand parameter indicative of the metabolic parameter, said controller receiving said metabolic demand parameter for generating said commands.

23. The pacemaker of claim 22 wherein said metabolic detector is arranged and constructed to detect minute volume as said metabolic parameter.

24. The pacemaker of claim 10 further comprising a transthoracic impedance detector for detecting a transthoracic impedance signal, said respiration detector deriving said respiration signal from said transthoracic impedance signal.

25. The pacemaker of claim 24 further comprising a metabolic demand detector for detecting a metabolic demand of said patient.

26. The pacemaker of claim 25 wherein said metabolic demand detector is arranged to detect a minute volume as said metabolic demand parameter.

27. The pacemaker of claim 26 wherein said metabolic demand detector is adapted to detect said minute volume from said transthoracic impedance signal.

28. The pacemaker of claim 27 wherein said controller is adapted to derive said base rate from said minute volume.

29. The pacemaker of claim 28 further comprising an exercise detector for detecting an exercise level of said patient.

30. The pacemaker of claim 29 wherein said adjusting means includes means that decrease the level of adjustment with increased exercise level.

31. The pacemaker of claim 29 wherein said exercise detector is adapted to detect said level of exercise from said metabolic demand.

32. The pacemaker of claim 10 further comprises a memory for storing an age of said patient.

33. The pacemaker of claim 32 wherein said adjusting circuit modifies the level of adjustment of said base rate with increased patient age.

34. The pacemaker of claim 10 further comprising a memory for storing a fitness level of said patient.

35. The pacemaker of claim 34 wherein said adjusting circuit is adapted to modify the level of adjustment of said rate based on said fitness level.

36. A method of controlling the pacing rate of a pacemaker implanted in a patient, said method comprising the steps of:

generating a base pacing parameter for said pacemaker;

detecting a respiration for the patient;

adjusting said base pacing parameter by increasing and decreasing said base pacing parameter in synchronism and cyclically with said respiration to derive an adjusted pacing parameter which follows said respiration; and generating pacing commands in accordance with said adjusted pacing parameter.

37. The method of claim 36 wherein said step of adjusting said base pacing parameter comprises changing said base pacing parameter between an upper and a lower limit in synchronism with said respiration.

38. The method of claim 37 wherein said step of adjusting comprises adding and subtracting a level P to and from said base pacing parameter.

39. The method of claim 38 wherein said step of adjusting comprises leaving said base pacing parameter unchanged between said adding and subtracting.

40. The method of claim 37 wherein said step of adjusting said base pacing parameter comprises the step of increasing said base pacing parameter gradually from a nominal value to a peak value.

41. The method of claim 40 wherein said step of increasing is followed by a step of gradually reducing said base rate from said peak value to a bottom value.

42. The method of claim 41 wherein said respiration has peaks and valleys and wherein said peak value is selected to substantially correspond timewise to said peak.

43. The method of claim 40 further comprising sensing a level of exercise of said patient, and wherein said peak value is changed in response to said level of exercise.

44. The method of claim 40 further comprising adjusting said peak value in accordance with an age of said patient.

45. The method of claim 40 further comprising adjusting said peak value in accordance with a physical fitness level of said patient.

46. The method of claim 40 further comprising sensing a metabolic demand of said patient, said base pacing parameter being dependent on said metabolic demand.

* * * * *